(12) United States Patent
Tichy et al.

(10) Patent No.: US 7,462,590 B2
(45) Date of Patent: Dec. 9, 2008

(54) AQUEOUS DISINFECTANTS AND STERILANTS COMPRISING A PEROXIDE/PERACID/TRANSITION METAL MIXTURE

(75) Inventors: Daryl J. Tichy, Orem, UT (US); Brian G. Larson, Orem, UT (US)

(73) Assignee: Solutions BioMed, LLC, Orem, UT (US)

( * ) Notice: Subject to any disclaimer, the term of this patent is extended or adjusted under 35 U.S.C. 154(b) by 366 days.

(21) Appl. No.: 11/361,841

(22) Filed: Feb. 24, 2006

(65) Prior Publication Data

US 2006/0198876 A1    Sep. 7, 2006

Related U.S. Application Data

(60) Provisional application No. 60/656,723, filed on Feb. 25, 2005.

(51) Int. Cl.
*C11D 7/18* (2006.01)
*C11D 3/48* (2006.01)

(52) U.S. Cl. .................. 510/372; 510/161; 510/199; 510/235; 510/238; 510/302; 510/309; 510/319; 510/362; 510/370; 510/367; 510/375; 510/382

(58) Field of Classification Search .............. 510/161, 510/199, 235, 238, 302, 309, 319, 362, 370, 510/367, 375, 382
See application file for complete search history.

(56) References Cited

U.S. PATENT DOCUMENTS

| | | |
|---|---|---|
| 716,077 A | 12/1902 | Morrin |
| 734,467 A | 7/1903 | Martien |
| 2,103,999 A | 12/1937 | Muller et al. |
| 2,304,104 A | 12/1942 | Klabunde et al. |
| 4,021,338 A | 5/1977 | Harkin |
| 4,297,298 A | 10/1981 | Crommelynch et al. |
| 4,311,598 A | 1/1982 | Verachtert |
| 4,321,255 A | 3/1982 | Boden |
| 4,414,127 A | 11/1983 | Fu |
| 4,655,975 A | 4/1987 | Snoble |
| 4,826,658 A | 5/1989 | Kay |
| 4,915,955 A | 4/1990 | Gomori |
| 5,349,083 A | 9/1994 | Brougham et al. |
| 5,357,636 A | 10/1994 | Dresdner et al. |
| 5,368,867 A | 11/1994 | Da Silva et al. |
| 5,419,908 A | 5/1995 | Richter et al. |
| 5,437,858 A | 8/1995 | Hungerbach et al. |
| 5,508,046 A | 4/1996 | Cosentino et al. |
| 5,563,132 A | 10/1996 | Bodaness |
| 5,709,870 A | 1/1998 | Yoshimura et al. |
| 5,824,267 A | 10/1998 | Kawasumi et al. |
| 5,945,032 A | 8/1999 | Breitenbach et al. |
| 5,951,993 A | 9/1999 | Scholz et al. |
| 5,977,403 A | 11/1999 | Byers |
| 5,997,585 A | 12/1999 | Scialla et al. |
| 6,027,469 A | 2/2000 | Johnson |
| 6,114,298 A | 9/2000 | Petri et al. |
| 6,197,814 B1 | 3/2001 | Arata |
| 6,200,946 B1 | 3/2001 | Blum et al. |
| 6,231,848 B1 | 5/2001 | Breitenbach et al. |
| 6,242,009 B1 | 6/2001 | Batarseh et al. |
| 6,257,253 B1 | 7/2001 | Lentsch et al. |
| 6,277,414 B1 | 8/2001 | Elhaik et al. |
| 6,302,968 B1 | 10/2001 | Baum et al. |
| 6,368,611 B1 | 4/2002 | Whitbourne et al. |
| 6,379,712 B1 | 4/2002 | Yan et al. |
| 6,436,342 B1 | 8/2002 | Petri et al. |
| 6,540,791 B1 | 4/2003 | Dias |
| 6,569,353 B1 | 5/2003 | Giletto et al. |
| 6,583,176 B2 | 6/2003 | Arata |
| 6,630,172 B2 | 10/2003 | Batarseh |
| 6,660,289 B1 | 12/2003 | Wilmotte et al. |
| 6,743,348 B2 | 6/2004 | Holladay et al. |
| 6,797,302 B1 | 9/2004 | Ben Yehuda et al. |
| 6,827,766 B2 | 12/2004 | Carnes et al. |
| 6,939,564 B2 | 9/2005 | Ranger et al. |

(Continued)

FOREIGN PATENT DOCUMENTS

GB    2189394    10/1987

(Continued)

OTHER PUBLICATIONS

U.S. Appl. No. 11/891,316; Tichy et al. filed Aug. 8, 2007.

(Continued)

*Primary Examiner*—Charles I Boyer
(74) *Attorney, Agent, or Firm*—Thorpe North & Western LLP

(57) ABSTRACT

The present invention is drawn to disinfectant or sterilant compositions and associated methods of use. In one embodiment, an aqueous disinfectant or sterilant composition can comprise an aqueous vehicle, including water, from 0.001 wt % to 50 wt % of a peracid, and from 0.001 wt % to 25 wt % of a peroxide. Additionally, from 0.001 ppm to 50,000 ppm by weight of a transition metal based on the aqueous vehicle content can also be present. The disinfectant composition can be used in the manufacture of disinfectant wipes, disinfectant gels, and disinfectant fogs. In one embodiment, the composition can be substantially free of aldehydes. Alternatively or additionally, the transition metal can be in the form of a colloidal transition metal.

93 Claims, No Drawings

U.S. PATENT DOCUMENTS

| | | |
|---|---|---|
| 6,939,566 B2 | 9/2005 | Batarseh et al. |
| 7,033,511 B2 | 4/2006 | Zawada et al. |
| 2003/0008797 A1 | 1/2003 | Hage et al. |
| 2003/0099717 A1 | 5/2003 | Cabrera |
| 2003/0235623 A1* | 12/2003 | Van Oosterom ............. 424/616 |
| 2004/0067159 A1 | 4/2004 | Carnes et al. |
| 2004/0170742 A1* | 9/2004 | Ben Yehuda et al. ........ 426/615 |
| 2004/0234569 A1 | 11/2004 | Nakada et al. |
| 2005/0013836 A1 | 1/2005 | Raad |
| 2005/0194357 A1 | 9/2005 | Liu et al. |
| 2005/0256017 A1 | 11/2005 | Dykstra |
| 2005/0256200 A1 | 11/2005 | Burkhart et al. |
| 2006/0035808 A1 | 2/2006 | Ahmed et al. |
| 2006/0182813 A1 | 8/2006 | Holladay |
| 2006/0198798 A1 | 9/2006 | Tichy et al. |
| 2006/0199752 A1 | 9/2006 | Tichy et al. |
| 2006/0240381 A1* | 10/2006 | Rizoiu et al. .................. 433/80 |
| 2006/0263239 A1 | 11/2006 | Tichy et al. |
| 2007/0048175 A1 | 3/2007 | Tichy et al. |
| 2007/0053850 A1 | 3/2007 | Tichy et al. |
| 2007/0059202 A1 | 3/2007 | Tichy et al. |
| 2007/0059255 A1 | 3/2007 | Tichy et al. |
| 2007/0254044 A1 | 11/2007 | Karandikar et al. |
| 2008/0000931 A1 | 1/2008 | Tichy et al. |

FOREIGN PATENT DOCUMENTS

| | | |
|---|---|---|
| WO | WO 03/080231 A1 | 10/2003 |
| WO | WO 2005/000324 A2 | 1/2005 |
| WO | WO 2006/079109 | 7/2006 |

OTHER PUBLICATIONS

Schuster, A. et al., "Persistent silver disinfectant for the environment: Myth and reality," Am. J. Infect. Control, Jun. 2003, pp. 309-311, vol. 32.

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by $Ag^+$ Coordination Ionspray Tandem Mass Spectrometry: Free Radical Pathways of Complex Decomposition," J. Am. Soc. Mass Spectrum, Apr. 2001, pp. 449-455, vol. 12 (4).

http://web.archive.org/web/20060217191603/http://sanosilbiotech.com/start_food.html, Virosil F&B, "Swift Virucidal with Swiss Precision," Feb. 17, 2006, 5 pages.

N. Surdeau et al., Sensitivity of bacterial biofilms and planktonic cells to a new antimicrobial agent, Oxsil 320N, Journal of Hospital Infection, 2006 62 487-493, www.sciencedirect.co.

The interaction of silver ions and hydrogen peroxide in the inactivation of *E coli*; a preliminary evaluation of a new long lasting residual drinking water disinfectant; Water Science and Technology vol. 31 No. 5-6 pp. 123-129 (1995).

* cited by examiner

AQUEOUS DISINFECTANTS AND STERILANTS COMPRISING A PEROXIDE/PERACID/TRANSITION METAL MIXTURE

This application claims the benefit of U.S. Provisional Application Ser. No. 60/656,723, filed on Feb. 25, 2005, which is incorporated herein by reference in its entirety.

FIELD OF THE INVENTION

The present invention is drawn to consumer safe compositions and associated delivery systems and methods for use in disinfecting and sterilizing surfaces.

BACKGROUND OF THE INVENTION

Disinfectant and sterilants, such as hard surface disinfectants and sterilants, are widely used in both domestic and professional settings. Generally, though both sterilants and disinfectants are used for the same purpose, i.e. to kill bacteria and/or viruses, etc., a sterilant composition exhibits a greater kill level compared to a disinfectant. This being stated, most applications require only disinfectant levels bacteria/virus reduction, though other applications benefit considerably from the use of sterilants. For example, in the medical/dental industries, hard surfaces such as floors, walls, countertops, medical/dental instruments and equipment, etc., need to be clean or even sterilized for safe patient care.

Exemplary of a commonly used hard surface cleaner is Lysol® disinfectant. Though Lysol® is effective for many applications, Lysol® is not as effective at reducing levels of bacteria as commercially available glutaraldehyde aqueous solutions. Glutaraldehyde aqueous solutions are widely used as disinfectants (and often as sterilants), and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, and even sterilants, it would be desirable to provide compositions that can exhibit even more effective bacteria kill levels, and at the same time be safer for the individuals using the disinfectant/sterilant.

SUMMARY OF THE INVENTION

It has been recognized that it would be desirable to provide liquid solution and dispersion disinfectants that are effective for cleaning surfaces, such as hard surfaces. In accordance with this, a disinfectant wipe comprising a fabric impregnated with an aqueous disinfectant composition. The aqueous disinfectant composition includes an aqueous vehicle. The aqueous vehicle includes water, from 0.001 wt % to 50 wt % of a peracid, and from 0.001 wt % to 25 wt % of a peroxide. In addition the aqueous disinfectant includes from 0.001 ppm to 50,000 ppm by weight of a transition metal based on the aqueous vehicle content.

Another embodiment provides a disinfectant gel. The disinfectant gel includes an aqueous vehicle, a transition metal, and a thickening agent. The aqueous vehicle includes water, from 0.001 wt % to 50 wt % of a peracid, and from 0.001 wt % to 25 wt % of a peroxide. The transition metal is present in the disinfectant gel at from 0.001 ppm to 50,000 ppm by weight based on the aqueous vehicle content.

Another embodiment provides a disinfectant fog. The disinfectant fog includes an aerosolized disinfectant composition. The disinfectant composition includes an aqueous vehicle and a transition metal. The aqueous vehicle comprises water, from 0.001 wt % to 50 wt % of a peracid, and from 0.001 wt % to 25 wt % of a peroxide. The transition metal is present in the disinfectant composition in amounts of from 0.001 ppm to 50,000 ppm by weight of a transition metal based on the aqueous vehicle content.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "solution" is also used throughout the specification to describe the liquid compositions of the present invention. However, as these "solutions" can include colloidal transition metals, these compositions can also be described as dispersions or suspensions. As the continuous phase is typically a solution, and the transition metal is optionally present as a colloid, for convenience, these compositions will typically be referred to as "solutions" herein.

The term "substantially free" when used with the disinfectant compositions of the present invention refers to the total absence of or near total absence of a specific compound or composition. For example when a composition is said to be substantially free of aldehydes, there are either no aldehydes in the composition or only trace amounts of aldehydes in the composition.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, an aqueous disinfectant or sterilant composition can comprise an aqueous vehicle, including water, from 0.001 wt % to 50 wt % of a peracid, and from 0.001 wt % to 25 wt % of a peroxide. Additionally, from 0.001 ppm to 50,000 ppm by weight of a transition metal based on the aqueous vehicle content can also be present. In one embodiment, the transition metal can be in a colloidal form, and in another embodiment, the transition metal can be in an ionic form. When the transition metal is in colloidal form, it is notable that there is typically an amount of ionic metal also present in solution. Preferably, the compositions of the present invention can be substantially free of aldehydes, such as glutaraldehyde. In fact, in one embodiment, the disinfectant or sterilant composition can include only ingredients that are food-grade, food safe, or safer for use than glutaraldehyde or even Lysol®), where all of the ingredients are present at concentrations that are generally safe for human contact that normally occurs during a cleaning activity. For example, though not required, the composition can be substantially free of disinfectant ingredients commonly present in many commercially available surface cleaners. Examples of non-food-grade ingredients which can be omitted from the disinfectants or sterilants of the present invention include, but are not limited to, aldehydes such as glutaraldehyde; chlorine-based disinfectants; chlorine and bromine-based disinfectants; iodophore-based disinfectants; phenolic-based disinfectants, quaternary ammonium-based disinfectants; and the like.

This being stated, even at these safe concentrations, disinfectant compositions of the present invention can provide kill levels equal to and in some cases greater than the non-food-grade compositions. In one embodiment, the food-grade compositions can provide kill levels of greater than log 4. In another embodiment that food grade compositions can provide kill levels of greater than log 5. In another embodiment the food grade compositions can provide kill levels of greater than log 6. In yet another embodiment, the food-grade compositions can provide kill levels of greater than log 7. In still another embodiment the food-grade compositions can provide kill levels of greater than log 8. It is of note that the kill levels can vary depending on the components of the composition as well as the targeted organism and the substrate being disinfected cleaned. In most cases, these log reduction kill levels can be achieved within 15 seconds of applying the disinfectant composition. Prolonged exposure of the target organisms to the disinfectant compositions generally yields increased kill levels, however generally at least a kill level of greater than log 4 can be achieved within 15 seconds of exposure. It is noted that the kill levels for each type of infection, e.g., bacteria, spores, viruses, parasites, funguses, molds, etc., is related to the general resistance of that organism. For example, spores are generally more difficult to kill than bacteria, and thus, the kill time is usually lengthier and log reduction is usually lower for spores than for many common types of bacteria. This being stated, compositions in accordance with embodiments of the present invention have been shown to kill certain spores at a log 6 reduction in 15 minutes, which is significantly more potent to these spores than anything currently known in the art, e.g., traditional glutaraldehyde solutions kill similar spores at less than a 1-log reduction in 15 minutes.

The aqueous vehicle can optionally include other ingredients, such as organic co-solvents. In particular, certain alcohols can be present. For example, alcohols, including aliphatic alcohols and other carbon-containing alcohols, having from 1 to 24 carbons ($C_1$-$C_{24}$ alcohol) can be used. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, it has been discovered that polyhydric alcohols can be particularly effective in enhancing the disinfectant and sterilant potency of the compositions of the present invention, as well as provide some degree of added stabilization. Without being limited by any particular theory, it is believed that the increased number of hydroxyl groups in the polyhydric alcohols enhance the potency of the disinfectant and sterilant solutions by interacting with the aqueous medium and the peracid thereby stabilizing the solution. The increase in the hydroxyl groups may also increase the number of hydroxyl radicals or groups in the disinfectant/sterilant solutions thereby further enhancing the potency or kill ability of the solutions/dispersions. Examples of polyhydric alcohols which can be used in the present invention include but are not limited to ethylene glycol (ethane-1,2-diol) glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z, 12Z-octadecadien-1-ol), elaidyl alcohol (9E-octadecen-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), combinations thereof and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. If the desire is to provide a food grade or more food safe composition, then alcohols can be selected that satisfy this requirement. The concentration of alcohol can vary over a wide range, such as from 0 to 95% by weight, but when present, can range from 0.001 wt % to 95 wt %, and more preferably, from 1 wt % to 50 wt %. Further, ranges of from about 5 wt % to 50 wt % can also be used, and still further, ranges from about 5 wt % to about 15 wt % can be also be used. As these ranges are merely exemplary, one skilled in the art could modify these ranges for a particular application, considering such things as whether alcohol selected for use is polyhydric, whether the alcohol is food grade, mixtures of alcohols, etc.

Regarding the transition metal, in accordance with the embodiments of the present invention, the metal can be in ionic form, e.g. a metal salt, and/or colloidal form. In one specific embodiment, the transition metal can be in a submicron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peracid. However, with colloidal metals, typically, the surface is usually more susceptible to such oxidation. Further, when colloidal metals are dispersed in a colloidal solution, there is often an amount of the metal in ionic or salt form that is also present in the suspension solution. For example, a colloidal silver may include a certain percentage of a silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, alloys thereof, and mixtures thereof. Silver is often the most preferred, depending on the application, the levels of kill that are desired or required, the type of pathogen being targeted, the substrate that is being cleaned, etc. For example, if cleaning a copper instrument or surface, there may be some advantage to using copper as the transition metal rather than silver.

Any of these embodiments can also benefit from the use of alloys. For example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present invention include but are not limited to copper-silver allows, silver-manganese alloys, Iron-copper alloys, chromium-silver alloys, gold-silver alloys, and magnesium-silver alloys.

The concentration of the metal content, including colloidal and ionic metal, that can be present in the solution is from 0.001 ppm to 50,000 ppm by weight, based on the content of the liquid vehicle as a whole. However, in another embodiment, the concentration of metal can be from 10 ppm to 1500 ppm by weight. Exemplary colloidal silvers that can be used include those sold by Solutions IE, Inc. under the tradenames CS Plus and C S Ultra. Other colloidal silver products that can be used as the silver source include ASAP, Sovereign Silver, Silver Max, and the like. If used in ionic form, preferred silver salts include but are not limited to silver nitrate, silver acetate, silver citrate, silver oxide, and silver carbonate. In one embodiment, the colloidal particles used in the present invention can have a particle size range of from 0.001 µm to 1.0 µm. In another embodiment the colloidal transition metal particles can have a size range of from 0.030 µm to 0.5 µm. In still another embodiment the average particle size is 0.35 µm to 0.45 µm. Though any colloidal silver solution that is functional for use in the formulations of the present invention can be used, in one embodiment, it can be desirable to use RO water as the suspension medium for the colloidal silver that is mixed with the other ingredients. In a more detailed aspect, the RO water can also be distilled, resulting in 18-20 MΩ water, though this is not required.

The peracid (or peroxyacid) can be any aliphatic or aromatic peroxyacid that is functional for disinfectant purposes in accordance with embodiments of the present invention. While any peroxyacid could be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid and mixtures thereof. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

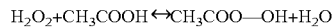

The peroxyacid portion of this formulation can range from about 0.001 wt % to about 50 wt %, but ranges from 0.001 wt % to 25 wt % are considered more desirable, and ranges from 1 wt % to 10 wt % are generally more preferred.

While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. The concentrations of the peroxide portion of this formulation can range from about 0.001 wt % to 25 wt %, but ranges of from 0.001 wt % to 10 wt %, and further, from 1 wt % to 3 wt % are often adequate for use.

The disinfectants and sterilant compositions of the present invention can be incorporated with other ingredients to form a variety of disinfectant and sterilant products including but not limited to hand cleansers, mouthwashes, surgical scrubs, body splashes, hand sanitizer gels and foams, disinfectant wipes, and similar personal care products. Additional types of products include disinfectant foams, creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The disinfectant compositions can also be used as disinfectant fogs and disinfectant mists. The present antibacterial compositions can be manufactured as dilute ready-to-use compositions, or as concentrates that are diluted prior to use. The various products in which the disinfectants are used may also include fragrances, depending on the nature of the product. For example, a pine or lemon fragrance may be desirable for use for kitchen cleaning wipes because of their appealing association with cleanliness to many consumers. Further, gels or aerosols may also be fragranced for similar or other reasons.

In one embodiment of the present invention, the disinfectant compositions are used to make disinfectant wipes. The disinfectant wipes of the present invention can be used to clean a variety of hard and other surfaces, including human hands and skin, medical instruments, countertops, floors, walls, windows, etc. The wipes of the present invention can be made of a variety of fabrics. For the purposes of the present invention fabrics are defined to include cloths and papers, as well as woven and non-woven materials. The woven or nonwoven fabrics can be made of suitable materials such as rayon, nylon, or cotton, combinations thereof. Examples of nonwoven fabrics are described in U.S. Pat. Nos. 3,786,615; 4,395,454; and 4,199,322; which are hereby incorporated by reference. The fabrics or papers can be impregnated with the disinfectant solution by any method known in the art. The wipes can be packaged in any manner known in the art including individual blister-packs or wrapped or stacked multi-packs.

In another embodiment, the disinfectant composition of the present invention is formulated into a gel or gelatinous sanitization composition. In addition to the disinfectant compositions, the gel sanitizers of the present invention can include a thickening or gelling agent, wherein "thickening agent" and "gelling agent" are used interchangeably. For the purposes of the present invention, the terms "gel" or "gelatinous" sanitization compositions refers to a disinfectant liquid substances that can have a viscosity from about 1,000 centipoise to about 100,000 centipoise, or from 2,000 centipoise to 50,000 centipoise in another embodiment, though these ranges are not intended to be limiting. For example, a hand gel may be considerably less viscous than a gel used for industrial cleaning or disinfectant purposes. Examples of gelling or thickening agents include but are not limited to natural gum such as guar and guar derivatives, a synthetic polymer, a clay, an oil, a wax, aloe vera gel, an acrylate homopolymer, an acrylate copolymer, a carbomer, cellulose, a cellulose derivative, algin, an algin derivative, a water-insoluble $C_8$-$C_{20}$ alcohol, carrageenan, fumed silica, mixtures thereof, and the like. The gelling agent can be present in the gelatinous sanitation composition in an amount from about 0.1 wt % to 50 wt % of the gelatinous composition. In another embodiment, the gelling agent is present in an amount from 0.25 wt % to 10 wt % of the gelatinous composition. The amount of gelling agent can be dependent on a variety of factors including the type of gelling agent and the desired viscosity of the gel. The gelatinous sanitizers can be used for a variety of applications including sanitization of human skin e.g., gel hand sanitizer, and hard surface sanitation. In one particular embodiment, the disinfectant composition can be mixed with natural aloe gel to form a disinfectant aloe formulation. Such a formulation would be useful for application to burns, skin infections, and other irritations. The aloe may act as a thickening agent, or may also include another thickening or gelling agent as described above, depending on the desired viscosity of the disinfectant gel.

In another embodiment, the disinfectant composition of the present invention can formulated into a disinfectant foam or foaming composition. The disinfectant foams or foaming compositions include the disinfectant composition and foaming agents. Any foaming agent known in the art can be used depending on the desired application and characteristics of the resulting disinfectant foam. As with the disinfectant composition, the disinfectant foams of the present invention can be used in both human (e.g. hand washing) and industrial applications.

In another embodiment, the disinfectant composition of the present invention can be in the form of a disinfectant aerosol or fog. Fogging, also referred to as thermal fogging, is the process by which disinfectants are aerosolized. The aerosol particles of the disinfectant are suspended within the air for a period of time in order to disinfect both the air itself and surfaces, including inaccessible parts of a structure such as air vents. The aerosolized particles of disinfectant can have a particle size of from about 5 µm to about 200 µm. In another embodiment, the aerosolized particle can have a particle size of from about 20 µm to about 150 µm. When the aerosolized disinfectant contains a colloidal transition metal, the aerosolized particles are typically of sufficient size to contain at least 1 of the colloidal transition metals, though typically, each aerosolized particle will contain multiple colloidal transition metal particles.

Fogging is often a last stage of a complete biosecurity program, and as such, can have a major part to play in disease prevention and control. Traditional fogging agents such as formaldehyde, glutaraldehyde, or glutaraldehyde can pose major health and safety issues to persons who come in contact with the disinfectant. As the disinfectants of the present invention can be formulated to use only food-grade ingredients, their use in disinfectant fogging is of great value. Most fogging machines work by using high volumes of air under great pressure to generate small droplets. The disinfectants compositions of the present invention are compatible with most standard fogging machines. Examples of suitable fogging machines include Dyna-Fog's® Thermal Foggers and Cold Foggers.

As a solution, the composition can be used as a liquid dispersion bath for objects such as instruments or as a spray for applying to less mobile objects. The disinfectant solution can also be used as a topical dressing or a mouthwash. In other words, any application method known by those skilled in the art can be utilized in accordance with embodiments of the present invention.

Additionally, though the compositions of the present invention are described primarily as general disinfectants and/or sterilants, it is recognized that there are many other possible applications. For example, without limitation, the compositions of the present invention can be used to kill bacteria, spores, viruses, parasites, funguses, and molds. As described, this powerful composition can be used against all of these types of organisms with relative to complete safety to humans and other mammals.

Because these compositions can be formulated to be very safe, e.g., including only food grade components in one embodiment, these compositions can be used in areas which extend well beyond their use as hard surface disinfectants and sterilants. Such product categories include both topically and internally applied products for both humans and animals. For example, these compositions can be used for antiseptics, burn treatments, diaper rash products, and various skin care products. Alternatively, these compositions can be used inside the mouth, such as for mouth washes, tooth pastes, and various other disinfecting solutions that are be employed in dental mold materials. As dental molds are known to spread significant disease in the dental industry, such use with dental molds can prevent or reduce the spread of pathogens from a patient's mouth to lab employees working with the finished molds. Still a further category of use includes application for antibiotic and antiviral purposes. These compositions can be formulated into lozenges or gums for application to the mouth and throat, and can even be administered orally, intramuscularly, intravenously, etc. Because of the kill levels that can be achieved, even when formulated with only food grade components, a wide range of pathogens, as well as some viruses, can be killed internally. Without being bound by any particular possibility, these compositions can be useful in killing various viruses such as HIV, SARS, West Nile, Bird Flu, and others.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Disinfectant

An aqueous disinfectant composition is prepared in accordance with embodiments of the present invention, which includes the following ingredients in approximate amounts:

85 wt % distilled water containing 600 ppm by weight colloidal silver;
9 wt % ethanol; and
6 wt % peroxyacetic acid.

To the composition is added a small amount, i.e. <3 wt % based on the aqueous composition as a whole, of hydrogen peroxide to stabilize the peroxyacetic acid. It is noted that there will be less than 600 ppm by weight of the colloidal silver when based on the aqueous vehicle content as a whole.

Example 2

Preparation of Disinfectant

An aqueous disinfectant composition is prepared in accordance with embodiments of the present invention, which includes the following ingredients in approximate amounts:

85 wt % distilled water containing 600 ppm by weight colloidal silver;
9 wt % isopropanol; and
6 wt % peroxypropanoic acid.

To the composition is added a small amount of sodium peroxide to stabilize the peroxypropanoic acid. It is noted that there will be less than 600 ppm by weight of the ionic silver when based on the aqueous vehicle content as a whole.

Example 3

Preparation of Disinfectant

An aqueous disinfectant composition is prepared in accordance with embodiments of the present invention, which includes the following ingredients in approximate amounts:

75 wt % RO water (reverse osmosis water) containing 1500 ppm by weight colloidal silver;
15 wt % ethanol; and
10 wt % peroxyacetic acid.

To the composition is added a small amount of hydrogen peroxide and acetic acid to the solution to stabilize the peracetic acid. It is noted that there will be less than 1500 ppm by weight of the colloidal silver when based on the aqueous vehicle content as a whole.

Example 4

Preparation of Disinfectant

An aqueous disinfectant composition is prepared in accordance with embodiments of the present invention, which includes the following ingredients in approximate amounts:

75 wt % distilled water containing 10000 ppm by weight colloidal silver;
20 wt % denatured alcohol; and
5 wt % peroxyformic acid.

Small amounts of hydrogen peroxide and formic acid are also added to the composition as a whole to stabilize the peroxyformic acid. It is noted that there will be less than 10000 ppm by weight of the colloidal silver when based on the aqueous vehicle content as a whole.

Example 5

Preparation of Disinfectant

An aqueous disinfectant composition is prepared in accordance with embodiments of the present invention, which includes the following ingredients in approximate amounts:

85 wt % distilled water containing 80 ppm by weight colloidal silver;
9 wt % ethanol; and
6 wt % peroxyacetic acid.

To the composition is added a small amount, i.e. <3 wt % based on the aqueous composition as a whole, of hydrogen peroxide to stabilize the peroxyacetic acid. It is noted that there will be less than 80 ppm by weight of the colloidal silver when based on the aqueous vehicle content as a whole.

Example 6

Kill-time Studies of *Staphylococcus aureus* Using Disinfectant of Example 1

A study was conducted to determine the antimicrobial activity of the colloidal silver-containing disinfectant of Example 1, when challenged with an organic load, on the test organism *Staphylococcus aureus*. This was accomplished by performing a standard suspension test on the disinfectant containing 5% v/v horse serum. A 15 second contact time was evaluated.

Specifically, the test suspension was prepared by growing a 5 ml culture of *Staphylococcus aureus*, ATCC 6538, in Todd Hewitt Broth at 37° C., for 20 hours. Five (5) ml of culture was pelleted by centrifugation, washed with 5 ml sterile 18 MΩ water, centrifuged again, and resuspended in a final volume of 5 ml sterile water.

A neutralizer was prepared that consisted of 9 ml tubes of 12.7 wt % Tween 80 (surfactant), 6.0 wt % Tamol, 1.7 wt % lecithin, 1 wt % peptone, and 0.1 wt % cystine, to which was added 10 pd of catalase solution (Sigma, C1 00, 42,300 units/mg).

The "Kill Time" procedure followed was as follows: A 9.9 ml aliquot of the disinfectant of Example 1 (containing 5% v/v horse serum) was placed in a sterile 20 mm×150 mm tube, and the tube was equilibrated in a 20° C. water bath. The tube of disinfectant was inoculated with 100 µl of the test organism suspension at time zero. After 15 seconds, 1 ml of the organism/disinfectant suspension was removed to 9 ml of neutralizer. After 2 minutes, the neutralized suspension was serially diluted (1:1×10, 1:1×10², 1:1×10³, etc.) in physiological saline solution (PSS). The number of viable organisms in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:$10^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 1a

| | Titer | | |
|---|---|---|---|
| | | Dilution | |
| | 1:1 × $10^5$ | 1:1 × $10^6$ | 1:1 × $10^7$ |
| Number of Colonies | TNC* TNC | TNC TNC | 111 89 |

*TNC—Too Numerous to Count

TABLE 1b

Disinfectant solution (Example 1 solution with 5% v/v horse serum) Dilution of *staphylococcus*/disinfectant suspension

| | Dilution | | |
|---|---|---|---|
| | 1:1 × $10^1$ | 1:1 × $10^2$ | 1:1 × $10^3$ |
| 15 Seconds | 0 0 | 0 0 | 0 0 |

TABLE 1c

Neutralization control

| | Dilution | |
|---|---|---|
| | undilute | 1:1 × $10^1$ |
| 15 Seconds | TNC TNC | 156 148 |

Sterilization controls indicated zero growth for the neutralizer, water, PSS, Columbia agar, disinfectant, and horse serum. Results of the titer showed a viable staphylococcus concentration of 1×$10^{10}$ organisms per ml in the original suspension. Inoculation of 9.9 ml of disinfectant with 100 µl of this suspension produced an initial concentration of 1×$10^8$ organisms per ml in the assay tube. Results from these procedures allowed log reduction (LR) and percent kill (PK) values to be calculated using the formulas: 1) LR=−Log(S/So) where S=concentration of viable organisms after 45 minutes; and So=the initial concentration of viable organisms at time zero; and 2) PK=(1−(S/So))×100. These values are shown below.

TABLE 2

| | Results | | |
|---|---|---|---|
| Solution | Contact Time | Log Reduction (LR) | Percent Kill (PK) |
| Disinfectant solution of Example 1 with 5% v/v horse serum | 15 sec | >7.00 | >99.99999 |

The neutralization control data indicated that the test solution was adequately neutralized. Observed counts were slightly greater than those expected, indicating no residual killing took place due to un-neutralized disinfectant. In general, the disinfectant solution tested here had high antimicrobial activity against *Staphylococcus aureus*. It is significant to note that this level of activity was achieved even though the disinfectant was premixed with an organic load consisting of 5% v/v horse serum. An organic load (such as 5% v/v horse serum) will often adversely affect the antimicrobial action of disinfectants. The solution of Example 1 was nevertheless able to effect greater than a 7 log reduction of viable organisms within 15 seconds, even in the presence of 5% v/v horse serum.

Example 7

Kill-time Studies of *Staphylococcus aureus* Using Lysol® Spray

A study was conducted to determine the antimicrobial activity of a Lysol® spray disinfectant on the test organism *Staphylococcus aureus*. This was accomplished by performing a standard suspension test. A 15 second contact time was evaluated.

Specifically, a test organism in the form of a test suspension was prepared by growing a 5 ml culture of *Staphylococcus aureus*, ATCC 6538 in Todd Hewitt Broth at 37° C., for 20 hr. Five (5) ml of culture was pelleted by centrifugation, washed with five ml sterile 18 MΩ water, centrifuged again, and resuspended in a final volume of five ml sterile water.

A neutralizer was also prepared that consisted of 9 ml tubes of 12.7 wt % Tween 80, 6.0 wt % Tamol, 1.7 lecithin, 1 wt % peptone, and 0.1 wt % cystine.

The "Kill Time" procedure followed was as follows: A 9.9 ml aliquot of the disinfectant (Lysol® Brand II Disinfectant, Spring Waterfall Scent, Lot # B4194-NJ2; 1413-A3) was placed in a sterile 20 mm×150 mm tube. The tube was equilibrated in a 20° C. water bath. The tube of disinfectant was inoculated with 100 µl of the test organism suspension at time zero. After 15 seconds, 1 ml of organism/disinfectant suspension was removed to 9 ml of neutralizer. After 2 minutes, the neutralized suspension was serially diluted (1:1×10, 1:1×$10^2$, 1:1×$10^3$, etc.) in physiological saline solution (PSS). The number of viable organisms in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:$10^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 3a

| | Titer | | |
|---|---|---|---|
| | Dilution | | |
| | $1{:}1 \times 10^5$ | $1{:}1 \times 10^6$ | $1{:}1 \times 10^7$ |
| Number of Colonies | TNC* TNC | 127 167 | 15 13 |

*TNC—Too Numerous to Count

TABLE 3b

| Disinfectant solution (Lysol ® Spray) Dilution of *staphylococcus*/disinfectant suspension | | | |
|---|---|---|---|
| | Dilution | | |
| | $1{:}1 \times 10^1$ | $1{:}1 \times 10^2$ | $1{:}1 \times 10^3$ |
| 15 Seconds | 0 0 | 0 0 | 0 0 |

TABLE 3c

| Neutralization control | | |
|---|---|---|
| | Dilution | |
| | undilute | $1{:}1 \times 10^1$ |
| 15 Seconds | TNC TNC | 76 72 |

Sterilization controls indicated zero growth for the neutralizer, water, PSS, Columbia agar, and disinfectant. Results of the titer showed a viable staphylococcus concentration of $1.47 \times 10^9$ organisms per ml in the original suspension. Inoculation of 9.9 ml of disinfectant with 100 µl of this suspension produced an initial concentration of $1.47 \times 10^7$ organisms per ml in the assay tube. Results from these procedures allowed log reduction (LR) and percent kill (PK) values to be calculated using the formulas: 1) $LR = -\text{Log}(S/S_o)$ where S=concentration of viable organisms after 45 minutes; and $S_o$=the initial concentration of viable organisms at time zero; and 2) $PK = (1 - (S/S_o)) \times 100$.

These values are shown in the Table 4 below.

TABLE 4

| Results | | | |
|---|---|---|---|
| Solution | Contact Time | Log Reduction (LR) | Percent Kill (PK) |
| Lysol ® Spray | 15 sec | >6.17 | >99.99993 |

The neutralization control data indicated that each test solution was adequately neutralized. Observed counts were slightly greater than those expected, indicating no residual killing took place due to un-neutralized disinfectant. In general, Lysol® Spray had high antimicrobial activity against *Staphylococcus aureus*. It was able to effect greater than a 6-log reduction of viable organisms within 15 seconds. As a note, this test was conducted without the horse serum organic load of Example 5.

In accordance with the present comparative example using Lysol®, it is to be noted that this example is a suspension example conducted in an enclosed environment. Because of the large amount of alcohol in Lysol®, Lysol® performs much better in the enclosed environment when compared to a typical open air use on a hard surface. Conversely, the compositions prepared in accordance with embodiments of the present invention, which can include a majority of water (which evaporates much less rapidly than alcohol), perform more similarly in suspension examples compared to open air hard surface applications. Thus, the comparison of the present Lysol® example to Example 6 shows Lysol® activity in a much more favorable light then would be present in actual use. For example, Reckitt Benckiser, who manufactures Lysol® products, advertises in their own Literature that Lysol® is able to kill 99.9% (3 $\text{Log}_{10}$ reduction) of bacteria (including *Staphylococcus aureous* (MRSA)) in 30 seconds, whereas the present suspension example shows a kill level of 99.9999% (6 $\text{Log}_{10}$ reductions) of *Staphylococcus aureous* in 15 seconds.

Example 8

Kill-Time Studies of Sporicidal Activity Using Disinfectant of Example 1

A study was conducted to determine the antimicrobial activity of the silver-containing disinfectant of Example 1 on bacterial endospores from the test organism *Bacillus subtilis*. This was accomplished by performing a standard kill-time suspension test using a suspension of *B. subtilis* endospores. In general, spores are much more difficult to kill than common bacteria.

The test organism in the form of a test suspension was prepared containing endospores from *Bacillus subtilis* (ATCC # 19659). The endospores were specifically prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 0.1 wt % cystine, to which 10 µl of catalase solution (Sigma, C100, 42,300 units/mg) was added immediately before use.

The "kill time" procedure was as follows: A 9.9 ml aliquot of the disinfectant was placed in a sterile glass culture tube. The tube was equilibrated in a 20° C. water bath. The tube of disinfectant was inoculated with 100 µl of the spore suspension at time zero. After 1 hour, 1 ml of spore/disinfectant suspension was removed to 9 ml of neutralizer. The tube was mixed thoroughly. After 2 minutes, the neutralized suspension was serially diluted ($1{:}1 \times 10$, $1{:}1 \times 10^2$, $1{:}1 \times 10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 μl of the 1:1×10$^5$ dilution of the titer. This produced about 200 CFU/ml in the tube, which was allowed to stand for 20 minutes prior to dilution and assay by membrane filtration using duplicate 1 ml samples.

The results are provided as follows:

TABLE 5a

Titer

| | Dilution | | |
|---|---|---|---|
| | 1:1 × 10$^6$ | 1:1 × 10$^7$ | 1:1 × 10$^8$ |
| Number of Colonies | TNC* TNC | 210 37 | 8 14 |

*TNC—Too Numerous to Count

TABLE 5b

Disinfectant solution (Example 1)
Dilution of B. subtilis spores/disinfectant suspension

| | Dilution | | |
|---|---|---|---|
| | 1:1 × 10$^2$ | 1:1 × 10$^3$ | 1:1 × 10$^4$ |
| 5 minutes | 13 18 | 4 2 | 0 0 |

TABLE 5c

Disinfectant solution (Example 1)
Dilution of B. subtilis spores/disinfectant suspension

| | Dilution | | | |
|---|---|---|---|---|
| | 1:1 × 10$^1$ | 1:1 × 10$^2$ | 1:1 × 10$^3$ | 1:1 × 10$^4$ |
| 10 minutes | 24 37 | 2 2 | 0 1 | 0 0 |

TABLE 5d

Disinfectant solution (Example 1)
Dilution of B. subtilis spores/disinfectant suspension

| | Dilution | | |
|---|---|---|---|
| | 1:1 × 10$^1$ | 1:1 × 10$^2$ | 1:1 × 10$^3$ |
| 15 minutes | 0 0 | 0 0 | 0 0 |

TABLE 5e

Neutralization control

| | Dilution | |
|---|---|---|
| | undilute | 1:1 × 10$^1$ |
| 15 Seconds | 185 214 | 12 25 |

Sterilization controls indicated zero growth for the water, PSS, Columbia agar, and disinfectant. Results of the titer showed a viable B. subtilis spore concentration of 1.24×10$^9$ spores per ml in the original suspension. Inoculation of 9.9 ml of disinfectant with 100 μl of this suspension produced an initial concentration of 1.24×10$^7$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 6.

TABLE 6

| | | Results | |
|---|---|---|---|
| Solution | Contact Time | Log Reduction (LR) | Percent Kill (PK) |
| Example 1 | 5 min | 3.90 | 99.9875 |
| Example 1 | 10 min | 4.61 | 99.9975 |
| Example 1 | 15 min | >6.09 | 99.99992 |

Neutralization control data revealed that the neutralizer was able to adequately neutralize this disinfectant. Observed counts were greater than those expected. The solution of Example 1 had relatively high sporicidal activity, producing greater than a 6-log reduction within 15 minutes. B. subtilis is a common species used in sporicidal testing and belongs to the same genus as the organism that causes anthrax. In other words, because of their genetic similarities, B. subtilis spores have been used as non-pathogenic surrogates for spores of Bacillus anthracis.

Example 9

Kill-time Studies of Francisella tularensis Using Disinfectant of Example 2

A study was conducted to determine the antimicrobial activity of the silver-containing disinfectant of Example 2 on Francisella tularensis bacteria, the etiologic agent of tularemia. This was accomplished by performing a standard kill-time suspension test using a suspension of fully virulent F. tularensis bacteria. As the organism is a CDC select agent, all tests were performed in a Biosafety Level 3 (BSL-3) laboratory by personnel trained in BSL-3 practices and procedures.

The test organism in the form of a test suspension was prepared containing F. tularensis bacteria (isolate#: 02-1103a). The suspension was prepared as follows: Four Trypticase Soy Agar plates with 0.1% cysteine and 5% sheep blood (TSACB) were lawn-inoculated from isolated colonies on a production plate that had been gram-stained to insure purity. The plates were incubated at 37° C. for 48 hours. The growth on each of four plates was scraped into suspension using three ml of physiological saline solution (PSS) and a bent loop. The suspension was pipetted into a 50 ml conical centrifuge tube. Suspensions from all four plates were collected into a single tube. The tube was centrifuged in an aerosol tight rotor at 3,845×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 µl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, 1:1×$10^2$, 1:1×$10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to TSACB agar plates. The plates were incubated at 37° C. for 72 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 µl of the 1:1×$10^5$ dilution of the titer. This produced about 7,110 colony forming units (CFU)/ml in the tube, which was allowed to stand for 20 minutes prior to dilution and assay by membrane filtration using duplicate 1 ml samples.

The results are provided as follows:

TABLE 7a

| | Titer | | | |
|---|---|---|---|---|
| | Dilution | | | |
| | 1:1 × $10^6$ | 1:1 × $10^7$ | 1:1 × $10^8$ | 1:1 × $10^9$ |
| Number of Colonies | TNC* TNC | TNC TNC | TNC TNC | 68 77 |

*TNC—Too Numerous to Count

TABLE 7b

| Disinfectant solution (Example 2) Dilution of F. tularensis/disinfectant suspension | | |
|---|---|---|
| | Dilution | |
| | 1:1 × $10^1$ | 1:1 × $10^2$ |
| 15 Seconds | 0 | 0 |
| | 0 | 0 |
| 30 Seconds | 0 | 0 |
| | 0 | 0 |

TABLE 7c

| Neutralization control | |
|---|---|
| Undiluted | 1:10 |
| TNC | 588 |
| TNC | 558 |

Results of the titer showed a viable F. tularensis concentration of 7.25×$10^{10}$ CFU per ml in the original suspension. Inoculation of 9.0 ml of disinfectant with 1.0 ml of this suspension produced an initial concentration of 7.25×$10^9$ CFU per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 8.

TABLE 8

| Results | | | |
|---|---|---|---|
| Solution | Contact Time | Log Reduction (LR) | Percent Kill (PK) |
| Example 2 | 15 Seconds | >8.86 | 99.99999986 |
| Example 2 | 30 Seconds | >8.86 | 99.99999986 |

Neutralization control data revealed counts that were similar to those expected; a mean of 573 CFU were obtained and about 711 CFU were expected. This indicates that the neutralizer solution employed successfully neutralized the disinfectant solution in these tests. The solution demonstrated a relatively rapid kill rate of F. tularensis. It was able to produce greater than an eight-log reduction within 15 seconds, which was complete kill in the system employed.

Example 10

Kill-time Studies of *Yersinia pestis* Using the Disinfectant of Example 2

A study was conducted to determine the antimicrobial activity of the silver-containing disinfectant of Example 2 on *Yersinia pestis* bacteria, the etiologic agent of plague. This was accomplished by performing a standard kill-time suspension test using a suspension of fully virulent *Y. pestis* bacteria. As the organism is a CDC select agent, all tests were performed in a Biosafety Level 3 (BSL-3) laboratory by personnel trained in BSL-3 practices and procedures.

The test organism in the form of a test suspension containing *Y. pestis* bacteria (isolate#: 83-1880a) was prepared as follows: Four Columbia Agar plates were lawn-inoculated from isolated colonies on a production plate that had been gram-stained to insure purity. The plates were incubated at 28° C. with 5% $CO_2$ for 48 hours. The growth on each of four plates was scraped into suspension using three ml of physiological saline solution (PSS) and a bent loop. The suspension was pipetted into a 50 ml conical centrifuge tube. Each plate was rinsed with an additional two ml of PSS, which was also added to the 50 ml tube. Suspensions from all four plates were collected into a single tube. The tube was centrifuged in an aerosol tight rotor at 3,845×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 µl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, $1:1\times10^2$, $1:1\times10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. with 5% $CO_2$ for 48 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 µl of the $1:1\times10^5$ dilution of the titer. This produced about 3,380 colony forming units (CFU)/ml in the tube, which was allowed to stand for 20 minutes prior to dilution and assay by membrane filtration using duplicate 1 ml samples.

The results are provided as follows:

TABLE 9a

| | Titer | | | |
|---|---|---|---|---|
| | Dilution | | | |
| | $1:1\times10^6$ | $1:1\times10^7$ | $1:1\times10^8$ | $1:1\times10^9$ |
| Number of Colonies | TNC* TNC | TNC TNC | 260 267 | 31 38 |

*TNC—Too Numerous to Count

TABLE 9b

Disinfectant solution (Example 2)
Dilution of *Y. pestis*/disinfectant suspension

| | Dilution | |
|---|---|---|
| | $1:1\times10^1$ | $1:1\times10^2$ |
| 15 Seconds | 0 0 | 0 0 |
| 30 Seconds | 0 0 | 0 0 |

TABLE 9c

| Neutralization control | |
|---|---|
| Undiluted | 1:10 |
| TNC | 53 |
| TNC | 60 |

Results of the titer showed a viable *Y pestis* concentration of $3.45\times10^{10}$ CFU per ml in the original suspension. Inoculation of 9.0 ml of disinfectant with 1.0 ml of this suspension produced an initial concentration of $3.45\times10^9$ CFU per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 10.

TABLE 10

| | Results | | |
|---|---|---|---|
| Solution | Contact Time | Log Reduction (LR) | Percent Kill (PK) |
| Example 2 | 15 Seconds | >8.54 | 99.9999997 |
| Example 2 | 30 Seconds | >8.54 | 99.9999997 |

Neutralization control data revealed counts that were similar to those expected; a mean of 57 CFU were obtained and about 338 CFU were expected. As this same neutralizer formulation successfully neutralized the disinfectant of Example 2 in tests with other organisms, studies were initiated to discover any *Y. pestis*-specific toxicity that might be inherent in this neutralizer. The disinfectant of Example 2 demonstrated a relatively rapid kill rate of *Y. pestis*. It was able to produce greater than eight-log reduction within 15 seconds, which was complete kill in the system employed.

Example 11

Kill-time Studies of *Brucella abortus* Using the Disinfectant of Example 2

A study was conducted to determine the antimicrobial activity of the silver-containing disinfectant of Example 2 on *Brucella abortus* bacteria, the etiologic agent of undulant fever or brucellosis. This was accomplished by performing a standard kill-time suspension test using a suspension of fully virulent *B. abortus* bacteria. As the organism is a CDC select agent, all tests were performed in a Biosafety Level 3 (BSL-3) laboratory by personnel trained in BSL-3 practices and procedures.

The test organism in the form of a test suspension containing *B. abortus* bacteria (698 strain 544) was prepared as follows: Four *Brucella* Blood Agar (BBA) plates were lawn-inoculated from isolated colonies on a production plate that had been gram-stained to insure purity. The plates were incubated at 37° C. with 5% $CO_2$ for 48 hours. The growth on each of four plates was scraped into suspension using three ml of physiological saline solution (PSS) and a bent loop. The suspension was pipetted into a 50 ml conical centrifuge tube. Each plate was rinsed with an additional two ml of PSS, which was also added to the 50 ml tube. Suspensions from all four plates were collected into a single tube. The tube was centrifuged in an aerosol tight rotor at 3,845 ×g for seven minutes. The supernatant solution was removed and the pellet was re-suspended in 4 ml of PSS. The suspension was held at 4° C. until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cysteine, and 500 mM Tris (pH 7.7), to which 100 µl of catalase solution (Sigma, C100, 42,300 units/mg) was added immediately before use.

The "kill time" procedure was as follows: A 9.9 ml aliquot of the disinfectant described in Example 2 was placed in a sterile glass culture tube. The tube was equilibrated in a 20° C. water bath. The tube of disinfectant was inoculated with 1.0 ml of the test organism suspension at time zero. After 15 seconds and 30 seconds 1 ml of test organism/disinfectant suspension was removed to 9 ml of neutralizer. The tube was mixed thoroughly. After 2 minutes, the neutralized suspension was serially diluted (1:10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. with 5% $CO_2$ for 48 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 100 ml of disinfectant with 100 μl of the 1:1×10$^6$ dilution of the titer. This produced about 290 colony forming units (CFU)/ml in the tube, which was allowed to stand for 20 minutes prior to dilution and assay by membrane filtration using duplicate 1 ml samples.

The results are provided as follows:

TABLE 11a

Titer

| | Dilution | | |
|---|---|---|---|
| | 1:1 × 10$^7$ | 1:1 × 10$^8$ | 1:1 × 10$^9$ |
| Number of Colonies | TNC* | 260 | 290 |
| | TNC | 267 | 301 |

*TNC—Too Numerous to Count

TABLE 11b

Disinfectant solution (Example 2)
Dilution of B. abortus/disinfectant suspension

| | Dilution | |
|---|---|---|
| | 1:1 × 10$^1$ | 1:1 × 10$^2$ |
| 15 Seconds | 1 | 0 |
| | 0 | 0 |
| 30 Seconds | 0 | 0 |
| | 0 | 0 |

TABLE 11c

Neutralization control

| Undiluted | 1:10 |
|---|---|
| TNC | 200 |
| TNC | 183 |

Results of the titer showed a viable B. abortus concentration of 2.96×10$^{11}$ CFU per ml in the original suspension. Inoculation of 9.0 ml of disinfectant with 1.0 ml of this suspension produced an initial concentration of 2.96×10$^{10}$ CFU per ml in the assay tube. Results from these procedures allowed log reduction (LR) and percent kill (PK) values to be calculated using the formulas: 1) LR=−Log(S/So) where S=concentration of viable organisms after the specified contact time, and So=the initial concentration of viable organisms at time zero; and 2) PK=(1−(S/So))×100. These values are shown below in Table 12.

TABLE 12

| | Results | | |
|---|---|---|---|
| Solution | Contact Time | Log Reduction (LR) | Percent Kill (PK) |
| Example 2 | 15 Seconds | >9.74 | 99.99999997 |
| Example 2 | 30 Seconds | >9.74 | 99.99999997 |

Neutralization control data revealed counts that were similar to those expected; a mean of 1,915 CFU were obtained and about 290 CFU were expected. This indicates that the neutralization solution employed successfully neutralized the disinfectant of Example 2 in these tests. The disinfectant of Example 2 demonstrated a relatively rapid kill rate of B. abortus. It was able to produce greater than nine-log reduction within 15 seconds, which was nearly complete kill in the system employed.

Example 12

Kill-time studies of *Bacillus anthracis* Using the Disinfectant of Example 2

A study was conducted to determine the antimicrobial activity of the silver-containing disinfectant of Example 2 on bacterial endospores from the test organism *Bacillus anthracis* bacteria. This was accomplished by performing a standard kill-time suspension test using purified endospores from a fully virulent B anthracis isolate. Because large concentrations of virulent spores were used, all tests were performed in a Biosafety Level 3 (BSL-3) laboratory by personnel trained in BSL-3 practices and procedures.

The test organism in the form of a test suspension containing endospores from B anthracis (A0256) was prepared from four 250 ml cultures grown in Leighton Doi medium in 2L Ehrlenmeyer flasks. The flasks were shaken at 100 RPM at 37° C. for 3-5 days until 90% sporulation was achieved, as monitored by phase-contrast microscopy. Spores were harvested and washed three times with sterile HPLC water, and stored at 4° C. overnight. Three additional washes were performed, allowing the suspension to stand at 4° C. overnight between each wash. The spores were re-suspended in a total of 80 ml of sterile HPLC water until used.

A neutralizer solution was also prepared that consisted of 9 ml tubes of 12.7 wt % Tween 80, 6.0 wt % Tamol, 1.7 wt % lecithin, 1 wt % peptone, 1.0 wt % cystine, and 500 mM Tris (pH 7.7), to which 100 μl of catalase solution (Sigma, C100, 42,300 units/mg) was added immediately before use.

The "kill time" procedure was as follows: A 4.5 ml aliquot of the disinfectant described in Example 2 was placed in a sterile glass culture tube. The tube was equilibrated in a 20° C. water bath. The tube of disinfectant was inoculated with 0.5 ml of the spore suspension at time zero. After 15 seconds and 30 seconds 1 ml of spore/disinfectant suspension was removed to 9 ml of neutralizer. The tube was mixed thoroughly. After 2 minutes, the neutralized suspension was serially diluted (1:10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9 ml of neutralizer and 1 ml of disinfectant with 100 μl of the $1:1\times10^5$ dilution of the titer. This produced about 360 colony forming units (CFU)/ml in the tube, which was allowed to stand for 20 minutes prior to dilution and assay by membrane filtration using duplicate 1 ml samples.

The results are provided as follows:

TABLE 13a

| | Titer | | | |
|---|---|---|---|---|
| | Dilution | | | |
| | $1:1\times10^6$ | $1:1\times10^7$ | $1:1\times10^8$ | $1:1\times10^9$ |
| Number of Colonies | TNC* TNC | TNC TNC | 34 40 | 1 4 |

*TNC—Too Numerous to Count

TABLE 13b

| Disinfectant solution (Example 2) | | | |
|---|---|---|---|
| Dilution of B. anthracis spores/disinfectant suspension | | | |
| | Dilution | | |
| | $1:1\times10^1$ | $1:1\times10^2$ | $1:1\times10^3$ |
| 15 Seconds | TNC TNC | 149 99 | 6 18 |
| 30 Seconds | 4 2 | 0 0 | — — |

TABLE 13c

| Neutralization control | |
|---|---|
| Undiluted | 1:10 |
| TNC TNC | 64 61 |

Results of the titer showed a viable B. anthracis spore concentration of $3.70\times10^9$ spores per ml in the original suspension. Inoculation of 4.5 ml of disinfectant with 1.0 ml of this suspension produced an initial concentration of $3.70\times10^8$ spores per ml in the assay tube. Results from these procedures allowed log reduction (LR) and percent kill (PK) values to be calculated using the formulas: 1) $LR=-Log(S/So)$ where S=concentration of viable organisms after the specified contact time, and So=the initial concentration of viable organisms at time zero; and 2) $PK=(1-(S/So))\times100$. These values are shown below in Table 14.

TABLE 14

| Results | | | |
|---|---|---|---|
| Solution | Contact Time | Log Reduction (LR) | Percent Kill (PK) |
| Example 2 | 15 Seconds | 4.48 | 99.997 |
| Example 2 | 30 Seconds | 7.09 | 99.999992 |

Neutralization control data revealed that the neutralizer was able to adequately neutralize this disinfectant. Observed counts were greater than those expected (63 vs. 36 respectively). The disinfectant of Example 2 had relatively rapid sporicidal activity against anthrax spores. It was able to produce greater than a seven log reduction in 30 seconds, which is close to complete kill in the system employed. The disinfectant of Example 2 displayed an extremely fast kill rate on B. anthracis spores, compared with other common chemical disinfectants. To put this in perspective, previous data using spores from this same isolate showing the alkaline glutaraldehyde (diluted to its minimum effective concentration of 1.5%) required 50 minutes to perform a six-log reduction.

Example 13

Kill-Time Studies of Sporicidal Activity Using 2.4% Alkaline Glutaraldehyde Disinfectant A study was conducted to determine the antimicrobial activity of a 2.4% alkaline glutaraldehyde disinfectant on bacterial endospores from the test organism Bacillus subtilis. Glutaraldehyde disinfectant solution is a common disinfectant used in hospitals to kill bacteria and other pathogens that might otherwise be difficult to kill. This study was carried out by performing a standard kill-time suspension test using a suspension of B. subtilis endospores. A 15 minute contact time was evaluated.

A test suspension containing endospores from Bacillus subtilis (ATCC # 19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4%, Lot #:2002247TP—diluted to 2.4 wt % with sterile water), was inoculated with 100 μl of the test organism suspension at time zero. After 15 min, 1 ml of spore/disinfectant suspension was removed to 9 ml of neutralizer. The tube was mixed thoroughly. After 2 minutes, the neutralized suspension was serially diluted ($1:1\times10$, $1:1\times10^2$, $1:1\times10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 μl of the $1:1\times10^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 15a

| | Titer | | |
|---|---|---|---|
| | Dilution | | |
| | $1:1 \times 10^6$ | $1:1 \times 10^7$ | $1:1 \times 10^8$ |
| Number of Colonies | TNC* TNC | 96 93 | 0 0 |

*TNC—Too Numerous to Count

TABLE 15b

Disinfectant solution (2.4 wt % alkaline glutaraldehyde disinfectant)
Dilution of *B. subtilis* spores/disinfectant suspension

| | Dilution | | | |
|---|---|---|---|---|
| | $1:1 \times 10^1$ | $1:1 \times 10^2$ | $1:1 \times 10^3$ | $1:1 \times 10^4$ |
| 15 minutes | TNC TNC | TNC TNC | TNC TNC | 259 52 |

TABLE 15C

| | Neutralization control | |
|---|---|---|
| | Dilution | |
| | $1:1 \times 10^1$ | $1:1 \times 10^2$ |
| 15 Seconds | 72 70 | 1 4 |

Sterilization controls indicated zero growth for the glutaraldehyde, sodium bisulfite, water, PSS, and Columbia agar. Results of the titer showed a viable *B. subtilis* spore concentration of $9.45 \times 10^8$ spores per ml in the original suspension. Inoculation of 9.9 ml of disinfectant with 100 µl of this suspension produced an initial concentration of $9.45 \times 10^6$ spores per ml in the assay tube. Results from these procedures allowed log reduction (LR) and percent kill (PK) values to be calculated using the formulas: 1) $LR = -\log(S/So)$ where S=concentration of viable organisms after 1 hour, and So=the initial concentration of viable organisms at time zero; and 2) $PK = (1-(S/So)) \times 100$. These values are shown below in Table 16.

TABLE 16

| | Results | | |
|---|---|---|---|
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes.

Example 14

Disinfectant Wipe

A disinfectant wipe is prepared using the disinfectant solution of Example 1. A nonwoven cotton fabric is impregnated with the disinfectant solution of Example 1. The wipes are prepared by placing a stack cotton fabric sheets in a container, saturating the fabric sheets with the disinfectant solution, and placing a cover over the container and sealing the container against evaporation of the disinfectant solution. Because the disinfectant solution of Example 1 includes colloidal silver, care is taken to make sure that each and every piece of nonwoven cotton fabric is exposed to not only the liquid, but to the solid particles as well.

Example 15

Disinfectant Gel

A disinfectant gel is prepared using the disinfectant solution of Example 2. The disinfectant of Example 2 is mixed with aloe vera gel forming a disinfectant gel. The gel is then applied to an infection on the skin of a subject. The disinfectant gel disinfects the skin and provides some relief from the irritation of the infection.

Example 16

Disinfectant Fog

The disinfectant composition of Example 2 is used to form a disinfectant fog. Using a thermal fogger from Dyno-Fog® the disinfectant composition is aerosolized into small droplets in a room in need of sterilization, e.g., a hospital room. The disinfectant fog is allowed to fill the room. The disinfectant fog sterilizes and disinfects the air and the hard surfaces in the room. After a period of about 40 minutes, the aerosolized particles are substantially settled out of the air and the room is substantially disinfected.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A disinfectant wipe, comprising a fabric impregnated with an aqueous disinfectant composition, said aqueous disinfectant composition, comprising:
   a) an aqueous vehicle, including:
      water;
      from 0.001 wt % to 50 wt % of a peracid; and
      from 0.001 wt % to 25 wt % of a peroxide, and
   b) from 0.001 ppm to 50,000 ppm by weight of a colloidal transition metal or alloy thereof based on the aqueous vehicle content.

2. A disinfectant wipe as in claim 1, wherein the fabric is a nonwoven fabric.

3. A disinfectant wipe as in claim 2, wherein the fabric includes nylon, rayon, cotton, or combinations thereof.

4. A disinfectant wipe as in claim 1, wherein the fabric is paper.

5. A disinfectant wipe as in claim 1, wherein the aqueous disinfectant composition is substantially free of aldehydes.

6. A disinfectant wipe as in claim 1, wherein the aqueous disinfectant composition is substantially free of chlorine and bromine-containing components.

7. A disinfectant wipe as in claim 1, wherein the aqueous disinfectant composition is substantially free of iodophore-containing components.

8. A disinfectant wipe as in claim 1, wherein the aqueous disinfectant composition is substantially free of phenolic-containing components.

9. A disinfectant wipe as in claim 1, wherein the aqueous disinfectant composition is substantially free of quaternary ammonium-containing components.

10. A disinfectant wipe as in claim 1, wherein the aqueous disinfectant composition further comprises from 0.001 wt % to 95 wt % $C_1$-$C_{24}$ alcohol as part of the aqueous vehicle.

11. A disinfectant wipe as in claim 10, wherein $C_1$-$C_{24}$ alcohol is selected from the group consisting of methanol, ethanol, propanols, butanols, pentanols, polyhydric alcohols, aromatic alcohols, and mixtures thereof.

12. A disinfectant wipe as in claim 1, wherein the colloidal transition metal or alloy thereof is a Group VI to Group XI transition metal or alloy thereof.

13. A disinfectant wipe as in claim 1, wherein the colloidal transition metal or alloy thereof is selected from the group consisting of ruthenium, rhodium, osmium, iridium, palladium, platinum, copper, gold, silver, alloys thereof, and mixtures thereof.

14. A disinfectant wipe as in claim 1, wherein the colloidal transition metal or alloy thereof is colloidal silver.

15. A disinfectant wipe as in claim 1, wherein the colloidal transition metal or alloy thereof has an average particle size of from 0.001 μm to 1.0 μm.

16. A disinfectant wipe as in claim 1, wherein the peracid is an aliphatic or aromatic peroxyacid.

17. A disinfectant wipe as in claim 1, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

18. A disinfectant wipe as in claim 1, wherein the peroxide is hydrogen peroxide.

19. A disinfectant wipe as in claim 1, wherein the peroxide is a metal peroxide selected from the group consisting of sodium peroxide, magnesium peroxide, calcium peroxide, barium peroxide, and strontium peroxide, and mixtures thereof.

20. A disinfectant wipe as in claim 1, wherein the peroxide is a peroxyhydrate.

21. A disinfectant wipe as in claim 1, wherein the peroxide is generated in situ from sodium percarbonate.

22. A disinfectant gel, comprising:
a) an aqueous vehicle including,
water;
from 0.001 wt % to 50 wt % of a peracid; and
from 0.001 wt % to 25 wt % of a peroxide, and
b) from 0.001 ppm to 50,000 ppm by weight of a colloidal transition metal or alloy thereof based on the aqueous vehicle content, and
c) a thickening agent.

23. A disinfectant gel as in claim 22, wherein the thickening agent is selected from the group consisting of natural gum selected from the group consisting of guar and guar derivatives, a synthetic polymer, a clay, an oil, a wax, aloe, aloe vera gel, an acrylate homopolymer, an acrylate copolymer, a carbomer, cellulose, a cellulose derivative, algin, an algin derivative, a water-insoluble $C_8$-$C_{20}$ alcohol, carrageenan, fumed silica, and mixtures thereof.

24. A disinfectant gel as in claim 22, wherein the thickening agent is present in an amount of from 0.1 wt % to 50 wt %.

25. A disinfectant gel as in claim 24, wherein the thickening agent is present in an amount of from 0.25 wt % to 10 wt %.

26. A disinfectant gel as in claim 22, wherein the disinfectant composition is substantially free of aldehydes.

27. A disinfectant gel as in claim 22, wherein the disinfectant composition is substantially free of chlorine and bromine-containing components.

28. A disinfectant gel as in claim 22, wherein the disinfectant composition is substantially free of iodophore-containing components.

29. A disinfectant gel as in claim 22, wherein the disinfectant composition is substantially free of phenolic-containing components.

30. A disinfectant gel as in claim 22, wherein the disinfectant composition is substantially free of quaternary ammonium-containing components.

31. A disinfectant gel as in claim 22, wherein the aqueous disinfectant further comprises from 0.001 wt % to 95 wt % $C_1$-$C_{24}$ alcohol as part of the aqueous vehicle.

32. A disinfectant gel as in claim 31, wherein $C_1$-$C_{24}$ alcohol is selected from the group consisting of methanol, ethanol, propanols, butanols, pentanols, polyhydric alcohols, aromatic alcohols, and mixtures thereof.

33. A disinfectant gel as in claim 22, wherein the colloidal transition metal is a Group VI to Group XI transition metal or alloy thereof.

34. A disinfectant gel as in claim 22, wherein the colloidal transition metal or alloy thereof is selected from the group consisting of ruthenium, rhodium, osmium, iridium, palladium, platinum, copper, gold, silver, alloys thereof, and mixtures thereof.

35. A disinfectant gel as in claim 22, wherein the colloidal transition metal or alloy thereof is colloidal silver.

36. A disinfectant gel as in claim 22, wherein the colloidal transition metal or alloy thereof has an average particle size of from 0.001 μm to 1.0 μm.

37. A disinfectant gel as in claim 22, wherein the peracid is an aliphatic or aromatic peroxyacid.

38. A disinfectant gel as in claim 22, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

39. A disinfectant gel in claim 22, wherein the peroxide is hydrogen peroxide.

40. A disinfectant gel as in claim 22, wherein the peroxide is a metal peroxide selected from the group consisting of sodium peroxide, magnesium peroxide, calcium peroxide, barium peroxide, and strontium peroxide, and mixtures thereof.

41. A disinfectant gel as in claim 22, wherein the peroxide is a peroxyhydrate.

42. A disinfectant gel as in claim 22, wherein the peroxide is generated in situ from sodium percarbonate.

43. A disinfectant gel as in claim 22, wherein the thickening agent is aloe or an aloe vera gel.

44. A disinfectant fog, comprising a aerosolized disinfectant composition, said disinfectant composition, comprising:
   a) an aqueous vehicle including,
      water;
      from 0.001 wt % to 50 wt % of a peracid; and
      from 0.001 wt % to 25 wt % of a peroxide, and
   b) from 0.001 ppm to 50,000 ppm by weight of a colloidal transition metal or alloy thereof based on the aqueous vehicle content.

45. A disinfectant fog as in claim 44, wherein the said aerosolized disinfectant has a particle size, said particle size being from about 5 μm to about 200 μm.

46. A disinfectant fog as in claim 45, wherein the particle size is from about 20 μm to about 150 μm.

47. A disinfectant fog as in claim 44, wherein the disinfectant composition is substantially free of aldehydes.

48. A disinfectant fog as in claim 44, wherein the disinfectant composition is substantially free of chlorine and bromine-containing components.

49. A disinfectant fog as in claim 44, wherein the disinfectant composition is substantially free of iodophore-containing components.

50. A disinfectant fog as in claim 44, wherein the disinfectant composition is substantially free of phenolic-containing components.

51. A disinfectant fog as in claim 44, wherein the disinfectant composition is substantially free of quaternary ammonium-containing components.

52. A disinfectant fog as in claim 44, wherein the aqueous disinfectant further comprises from 0.001 wt % to 95 wt % $C_1$-$C_{24}$ alcohol as part of the aqueous vehicle.

53. A disinfectant fog as in claim 52, wherein $C_1$-$C_{24}$ alcohol is selected from the group consisting of methanol, ethanol, propanols, butanols, pentanols, polyhydric alcohols, and mixtures thereof.

54. A disinfectant fog as in claim 44, wherein the colloidal transition metal or alloy thereof is a Group VI to Group XI transition metal or alloy thereof.

55. A disinfectant fog as in claim 44, wherein the colloidal transition metal or alloy thereof is selected from the group consisting of ruthenium, rhodium, osmium, iridium, palladium, platinum, copper, gold, silver, alloys thereof, and mixtures thereof.

56. A disinfectant fog as in claim 44, wherein the colloidal transition metal or alloy thereof is colloidal silver.

57. A disinfectant fog as in claim 44, wherein the colloidal transition metal or alloy thereof has an average particle size of from 0.001 μm to 1.0 μm.

58. A disinfectant fog as in claim 44, wherein the peracid is an aliphatic or aromatic peroxyacid.

59. A disinfectant fog as in claim 44, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

60. A disinfectant fog as in claim 44, wherein the peroxide is hydrogen peroxide.

61. A disinfectant fog as in claim 44, wherein the peroxide is a metal peroxide selected from the group consisting of sodium peroxide, magnesium peroxide, calcium peroxide, barium peroxide, and strontium peroxide, and mixtures thereof.

62. A disinfectant fog as in claim 44, wherein the peroxide is a peroxyhydrate.

63. A disinfectant fog as in claim 44, wherein the peroxide is generated in situ from sodium percarbonate.

64. A disinfectant foam, comprising:
   a) an aqueous vehicle including,
      water;
      from 0.001 wt % to 50 wt % of a peracid; and
      from 0.001 wt % to 25 wt % of a peroxide, and
   b) from 0.001 ppm to 50,000 ppm by weight of a colloidal transition metal or alloy thereof based on the aqueous vehicle content, and
   c) a foaming agent.

65. A disinfectant foam as in claim 64, wherein the disinfectant composition is substantially free of aldehydes.

66. A disinfectant foam as in claim 64, wherein the disinfectant composition is substantially free of chlorine and bromine-containing components.

67. A disinfectant foam as in claim 64, wherein the disinfectant composition is substantially free of iodophore-containing components.

68. A disinfectant foam as in claim 64, wherein the disinfectant composition is substantially free of phenolic-containing components.

69. A disinfectant foam as in claim 64, wherein the disinfectant composition is substantially free of quaternary ammonium-containing components.

70. A disinfectant foam as in claim 64, wherein the aqueous disinfectant further comprises from 0.001 wt % to 95 wt % $C_1$-$C_{24}$ alcohol as part of the aqueous vehicle.

71. A disinfectant foam as in claim 70, wherein $C_1$-$C_{24}$ alcohol is selected from the group consisting of methanol, ethanol, propanols, butanols, pentanols, polyhydric alcohols, and mixtures thereof.

72. A disinfectant foam as in claim 64, wherein the colloidal transition metal or alloy thereof is a Group VI to Group XI transition metal or alloy thereof.

73. A disinfectant foam as in claim 64, wherein the colloidal transition metal or alloy thereof is selected from the group consisting of ruthenium, rhodium, osmium, iridium, palladium, platinum, copper, gold, silver, alloys thereof, and mixtures thereof.

74. A disinfectant foam as in claim 64, wherein the colloidal transition metal or alloy thereof is colloidal silver.

75. A disinfectant foam as in claim 64, wherein the colloidal transition metal or alloy thereof has an average particle size of from 0.001 μm to 1.0 μm.

76. A disinfectant foam as in claim 64, wherein the peracid is an aliphatic or aromatic peroxyacid.

77. A disinfectant foam as in claim 64, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

78. A disinfectant foam as in claim 64, wherein the peroxide is hydrogen peroxide.

79. A disinfectant foam as in claim 64, wherein the peroxide is a metal peroxide selected from the group consisting of sodium peroxide, magnesium peroxide, calcium peroxide, barium peroxide, and strontium peroxide, and mixtures thereof.

80. A disinfectant foam as in claim 64, wherein the peroxide is a peroxyhydrate.

81. A disinfectant foam as in claim 64, wherein the peroxide is generated in situ from sodium percarbonate.

82. A disinfectant gel, comprising:
   a) an aqueous vehicle including,
      water;
      from 0.001 wt % to 50 wt % of a peracid; and
      from 0.001 wt % to 25 wt % of a peroxide, and b) from 0.001 ppm to 50,000 ppm by weight of a transition metal or alloy thereof based on the aqueous vehicle content, and c) a thickening agent wherein the disinfectant gel has a viscosity of 1000 centipoise to 100,000 centipoise.

83. A disinfectant gel as in claim 82, wherein the thickening agent is selected from the group consisting of natural gum selected from the group consisting of guar and guar derivatives, a synthetic polymer, a clay, an oil, a wax, aloe, aloe vera gel, an acrylate homopolymer, an acrylate copolymer, a carbomer, cellulose, a cellulose derivative, algin, an algin derivative, a water-insoluble $C_8$-$C_{20}$ alcohol, carrageenan, fumed silica, and mixtures thereof.

84. A disinfectant gel as in claim 82, wherein the thickening agent is present in an amount of from 0.1 wt % to 50 wt %.

85. A disinfectant gel as in claim 82, wherein the aqueous disinfectant further comprises from 0.001 wt % to 95 wt % $C_1$-$C_{24}$ alcohol as part of the aqueous vehicle.

86. A disinfectant gel as in claim 85, wherein $C_1$-$C_{24}$ alcohol is selected from the group consisting of methanol, ethanol, propanols, butanols, pentanols, polyhydric alcohols, aromatic alcohols, and mixtures thereof.

87. A disinfectant gel as in claim 82, wherein the transition metal is a Group VI to Group XI transition metal or alloy thereof.

88. A disinfectant gel as in claim 82, wherein the transition metal or alloy thereof is selected from group consisting ruthenium, rhodium, osmium, iridium, palladium, platinum, copper, gold, silver, alloys thereof, and mixtures thereof.

89. A disinfectant gel as in claim 82, wherein the transition metal or alloy thereof is a colloidal transition metal or alloy thereof.

90. A disinfectant gel as in claim 89, wherein the colloidal transition metal or alloy thereof is colloidal silver.

91. A disinfectant gel as in claim 82, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

92. A disinfectant gel as in claim 82, wherein the peroxide is hydrogen peroxide.

93. A disinfectant gel as in claim 82, wherein the gel has a viscosity of 2000 centipoise to 50,000 centipoise.

* * * * *